United States Patent
Baik et al.

(10) Patent No.: US 8,377,434 B2
(45) Date of Patent: Feb. 19, 2013

(54) COSMETIC COMPOSITION FOR EXFOLIATING SKIN KERATIN

(75) Inventors: Seung Jae Baik, Seoul (KR); Beung Young Kang, Seoul (KR); Eun Joo Kim, Suwon-shi (KR)

(73) Assignee: Amorepacific Corporation, Seoul (KR)

( * ) Notice: Subject to any disclaimer, the term of this patent is extended or adjusted under 35 U.S.C. 154(b) by 1148 days.

(21) Appl. No.: 11/720,281

(22) PCT Filed: Nov. 28, 2006

(86) PCT No.: PCT/KR2006/005055
§ 371 (c)(1), (2), (4) Date: Jul. 9, 2007

(87) PCT Pub. No.: WO2008/013342
PCT Pub. Date: Jan. 31, 2008

(65) Prior Publication Data
US 2010/0254969 A1 Oct. 7, 2010

(30) Foreign Application Priority Data
Jul. 27, 2006 (KR) .................. 10-2006-0070765

(51) Int. Cl.
*A61K 38/43* (2006.01)
(52) U.S. Cl. .................................... 424/94.65
(58) Field of Classification Search .......... None
See application file for complete search history.

(56) References Cited

U.S. PATENT DOCUMENTS

| 5,866,142 A * | 2/1999 | Riordan ............. 424/401 |
| 6,413,525 B1 | 7/2002 | Mammone et al. |
| 2004/0081681 A1 * | 4/2004 | Vromen ............. 424/449 |
| 2006/0134155 A1 * | 6/2006 | Dryer et al. ............. 424/401 |

FOREIGN PATENT DOCUMENTS

| JP | 09-2861715 | * | 4/1997 |
| JP | 2002-544154 A | | 12/2002 |
| JP | 2004-523532 A | | 8/2004 |
| JP | 2006-160711 A | | 6/2006 |
| KR | 10-2006-0072569 A | | 6/2006 |
| WO | WO 2004/093865 | | 11/2004 |

OTHER PUBLICATIONS

Japanese Patent Office, Office Action in corresponding JP Application No. 2009-521684 issued Mar. 29, 2012, English translation.
Fragrance Journal, vol. 26, p. 39-44 (1998), English Abstract provided in article.

* cited by examiner

*Primary Examiner* — Allison Ford
*Assistant Examiner* — Paul D. Pyla
(74) *Attorney, Agent, or Firm* — Sughrue Mion, PLLC

(57) ABSTRACT

The present invention relates to a cosmetic composition containing enzymes, and more particularly to a cosmetic composition, which contains, as active ingredients, 1) papain, and 2) at least one selected from the group consisting of theanine and N-acetyl glucosamine, and thus functions to control the skin turnover cycle and promote the exfoliation of skin keratin.

4 Claims, 4 Drawing Sheets
(2 of 4 Drawing Sheet(s) Filed in Color)

BEFORE USE   AFTER ONE WEEK OF USE

COSMETIC COMPOSITION FOR EXFOLIATING SKIN KERATIN

TECHNICAL FIELD

The present invention relates to a cosmetic composition containing enzymes, and more particularly to a cosmetic composition, which contains, as active ingredients, 1) papain and 2) at least one selected from the group consisting of theanine and N-acetyl glucosamine, and thus functions to controls the skin turnover cycle and promote the exfoliation of skin keratin.

BACKGROUND ART

The horny layer is the most external layer contacting with the exterior and protects the skin and body from physical and chemical hazard. The horny layer consists of 50% protein (called "keratin"), 20% fat, 23% water-soluble substance and 7% water. Because skin cells continue to be produced, old skin cells gradually move up to the horny layer, and the cells arriving at the horny layer are flattened dead cells, called "keratins". Millions of dead keratinocytes are removed from the skin daily and replaced with new keratinocytes (skin turnover). The term "peeling" refers to peeling a layer of dead cells from the skin epidermis so as to renew the skin. The skin naturally forms the turnover cycle where old keratin is removed by itself and a new skin moves up. However, due to aging or environmental conditions, such as drying, UV light and stress, old keratin remains without being naturally removed. For this reason, peeling as an artificial method is used to remove old keratin, such that the skin renewal cycle is restored and fresh cells produced in a basal layer is moved upward, thus making the skin clear and clean.

Cosmetics for such peeling will now be described.

(1) Chemical Peeling Products

Chemical peeling products are products containing acid components and can show the most rapid effect. The principle of chemical peeling is applied to loosen the linkage between keratin in a thick horny layer on the skin by the action of acid, such that excessive keratin, which has not been regularly removed, is softened such that it is well removed by, for example, facial washing. Chemical peeling agents are also most frequently used in dermatological peeling.

When a chemical peeling product is used in a home, it is important to previously examine the kind and content of acid used and to select a product suitable for the skin. Also, because old keratin is artificially removed, the amount of keratin is temporarily reduced, such that the protection of the skin from the external environment can become weak. For this reason, when a person moves during the daytime after he uses a peeling product, it is preferable to use a UV screening agent together with the peeling product.

Active ingredients, which are mainly used in chemical peeling, are as follows.

(a) AHA (Alpha Hydroxy Acid)

AHA is the most typical chemical component for removing keratin, helps to remove the linkage between keratins in the horny layer by the action of acid, and shows the effect of softening keratin. Specifically, components corresponding to AHA are as follows.

Glycolic acid: This is representative of AHA and is most frequently used in cosmetics. It has excellent skin permeability and an excellent ability to remove keratin. Also, it is used mainly in dermatology.

Lactic acid: This is a natural moisturizing factor on the human skin surface and is frequently used next to glycolic acid in cosmetics. It is extracted from sour milk, tomato juice and the like and is used in dermatology.

In addition, other examples of AHA include malic acid extracted from apples, citric acid from oranges, and tartaric acid from grape wine.

(b) BHA (Beta Hydroxy Acid)

BHA is a typical chemical component for removing keratin, like AHA, and a BHA component, which can be most frequently seen in cosmetics, is salicylic acid. Because BHA is oil soluble, unlike AHA, it effectively removes keratins excessively deposited at acne sites and easily penetrates into skin sites, which have increased sebum secretion and acne formation. Thus, it is frequently used in products for acne. Such chemical agents for removing keratin can show a good effect within a short period of time, but have disadvantages in that they tend to irritate the skin and their effect is not long-lasting.

(c) Enzymes

Because the horny layer contains much protein, the use of proteases can provide the effect of cutting the linkage between keratins present in the horny layer. This principle is applied to remove either old keratins coming from the exterior or non-uniform old keratins. Typically used enzymes include papain enzyme as vegetable protease. Keratin removal by enzyme shows low irritation, and thus is useful for controlling keratin in a sensitive skin, but has a disadvantage in that it is difficult to stabilize enzyme activity in cosmetics.

(2) Physical Peeling Products

Physical peeling products include various products, including scrub agents that remove keratin by causing friction with grains, and recent microdermabrasion products that employ microparticles along with additive active ingredients. The microdermabrasion products show the effect of removing old keratin by applying microparticles on the skin and then applying physical stimulation with hands. In dermatology, the skin is peeled off either by applying physical stimulation using an abrasion machine instead of using hands or by spraying microparticles directly on the skin using strong pressure. The physical peeling products are various depending on the shape and size of microparticles, but are products that apply physical stimulation, and thus it is necessary to select products containing particles suitable for skin sensitivity.

Keratinocytes are continuously formed, but old keratinocytes in the outermost layer are peeled off, and thus a layer of keratinocytes maintains a constant thickness. This phenomenon that the location of new cell layers changes is called "turnover". Epidermal turnover in the normal skin takes about 4 weeks, although it changes depending on site or age. When this horny layer remains on the skin without being normally peeled off, the horny layer becomes thick and the facial color becomes dark. Also, impurities on the skin surface or in hair follicles are oxidized or degraded by oxygen or microorganisms and cause skin troubles such as inflammation. The main component of such impurities is keratin, which remains on the skin surface even after cells are dead, and proteins in sweat remain on the skin surface after the sweat comes out. Because keratin has high molecular weight and is insoluble and not easily degraded, it is not easily removed with a cleaning agent alone, but it can be effectively removed by degrading it into small fragments using enzyme. The use of stable protease can remove a keratin layer attached to the skin surface and make the skin softer.

Typical examples of proteases, which have recently been used in cosmetics until recently, include papain, bromelain and the like that are proteases of plant origin. However, it is known that such proteases do not effectively degrade keratin and lose their activity during extraction and transport processes or do not maintain their activity over a long period of time. Moreover, alpha hydroxy acid that is used for the purpose of effectively keratin on the skin surface shows a tendency to gradually decrease, because it causes skin irritation due to low pH and weakens the skin surface upon repeated use.

DISCLOSURE

Technical Problem

The present inventors have studied a more fundamental mechanism of skin cell production and exfoliation and studied the combination and concentration of enzymes, which maintain the excellent skin safety of papain through the control of turnover cycle of skin cells and, at the same time, provide a high effect of peeling keratin, and also maintain the effect of the enzymes for a long period of time. As a result, the present inventors have found that the combined use of papain and theanine and/or N-acetyl glucosamine, which show the optimal efficacy in each phase, can safely and effectively remove keratins that are dead cells on the skin, thereby completing the present invention.

Accordingly, it is an object of the present invention to provide a cosmetic composition containing, as active ingredients, papain and theanine and/or N-acetyl glucosamine.

Technical Solution

To achieve the above object, the present invention provides a cosmetic composition, which contains, as active ingredients, 1) papain, and 2) at least one selected from the group consisting of theanine and/or N-acetyl glucosamine, and thus functions to control the skin turnover cycle and promote the exfoliation of skin keratin.

Hereinafter, the present invention will be described in further detail.

The present invention relates to an enzyme combination for increasing the function of proteases safe to the skin. Papain, which is well known in the art, is a vegetable enzyme obtained from papaya. It is a papaya enzyme having the ability to dissolve keratin and removes lipid peroxide or contaminated keratin. The present invention aims to use such papain in combination with N-acetyl glucosamine and theanine, an amino acid extracted from green tea, to increase a keratin exfoliation effect and, at the same time, maintain skin safety. Existing products for exfoliating keratin using enzyme have depended mainly on the keratin exfoliation function of papain enzyme on the epidermis. However, for a more fundamental exfoliation of keratin, not only the exfoliation of keratin on the epidermis, but also the production and differentiation of new cells in the granular layer and basal layer of the skin, should be activated such that skin turnover can be promoted and skin homeostasis can be maintained. N-acetyl glucosamine is greatly helpful in the formation and activity of new cells in the basal layer, and theanine functions to stimulate the differentiation of skin cells in the granular layer of the skin.

The function of each component of the cosmetic composition according to the present invention will now be described in further detail. N-acetyl glucosamine is glucosamine in a stable form. N-acetyl glucosamine inhibits the glycosylation of pro-tyrosinase, which is a process important in the excessive formation of melanine in skin cells damaged by UV light. Through in vivo and ex vivo studies, the present inventors have found that N-acetyl glucosamine is effective in improving excessive pigmentation, skin tone and barrier function. N-acetyl glucosamine was found to promote the production of hyaluronic acid, which is important in skin hydration and increases the expression of collagen. The improvement of skin hydration in human beings reduces the appearance of fine lines and wrinkles on a face, particularly eye sites. It is thought that improved skin tone and hydration result not only from an improvement in the collagen structure, but also from the action of N-acetyl glucosamine in the synthesis of hyaluronic acid. When N-acetyl glucosamine having such functions is used together with a product for keratin exfoliation, it will be greatly helpful in the production and activity of cells in the basal layer of the skin, resulting in the promotion of skin turnover.

Theanine (green tea amino acid), which is used in the present invention, is a unique amino acid extracted from green tea, has an excellent ability to provide long-term hydration and also has an effect on skin renewal. It pushes up healthy cells onto the skin through improved skin renewal capability (that is, reduces the skin turnover cycle), and this effect is helpful not only in the exfoliation of keratin, but also in the maintenance of skin homeostasis.

The present invention provides a cosmetic composition for the exfoliation of keratin, which contains, as active ingredients, 0.1-5.0 wt %, based on the total weight of the cosmetic composition, of papain, 0.1-5.0 wt % of theanine and/or 0.1-5.0 wt % of N-acetyl glucosamine.

If the content of papain is less than 0.1 wt %, it will not show a substantial effect on keratin exfoliation, and if it is more than 5.0 wt %, it will cause the risk of skin irritation. If the content of theanine is less than 0.1 wt %, it will not stimulate the differentiation of skin cells in the granular layer of the skin, and if it exceeds 5.0 wt %, it will cause problems of skin irritation and discoloration/deterioration.

The papain component mainly functions to soften and exfoliate keratin on the epidermis, and the theanine component mainly functions to accelerate skin turnover through the stimulation of cell differentiation in the granular layer of the skin. N-acetyl glucosamine serves to smooth the supply of cells to the granular layer and epidermis of the skin by promoting the production and activity of cells in the basal layer. Thus, it was found through a skin test that, when the papain component was used in combination with N-acetyl glucosamine and theanine extracted from green tea, a keratin exfoliation effect was rapidly increased. The inventive cosmetic composition prepared by combining such components with each other could safely and effectively remove keratins that are dead cells on the skin. That is, through a balanced circulation of three phases, the cosmetic composition maintains skin homeostasis and, at the same time, safely and effectively exfoliates skin keratin and maintains health. The cosmetic composition according to the present invention is the result of studies on a more fundamental mechanism associated with the production and exfoliation of skin cells and has an increased effect resulting from the combination of components showing the optimal efficacy in each phase.

The inventive cosmetic composition for the exfoliation of keratin may further comprise, in addition to the above active ingredients, additional additives which are conventionally used in the art.

DESCRIPTION OF DRAWINGS

The patent or application file contains at least one drawing executed in color. Copies of this patent or patent application publication with color drawing(s) will be provided by the Office upon receipt and payment of the necessary fee.

In FIG. 1, deep fluorescence means that the exfoliation of keratin is relatively insufficient. #S: Comparative Example 1, #P: Comparative Example 2, #PT: Example 1, #PN: Example 2, #PNT: Example 3, and #B: control.

MODE FOR INVENTION

Figure 1:
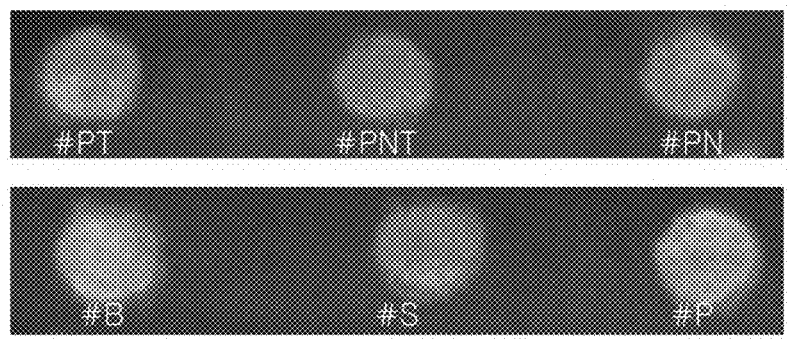
FIG. 1 is a photograph made by staining keratin with a fluorescent dye, applying samples on the stained keratin and photographing the samples, in order to examine the keratin-exfoliating abilities of cosmetic compositions prepared in Examples 1 to 3 and Comparative Examples 1 and 2.

Hereinafter, the construction and effect of the present invention will be described in further detail with reference to examples and test examples. It is to be understood, however, that these examples are illustrative only and the scope of the present invention is not limited thereto.

Examples 1 to 3 and Comparative Examples 1 and 2

Cosmetic emulsions of Examples 1-3 and Comparative Examples 1-2 were prepared according to the compositions shown in Table 1 below (unit: wt %). With respect to a process for preparing the cosmetic compositions, squalane and polysorbate 60 were mixed with each other to prepare an oil phase, and the remaining components were added to purified water to prepare an aqueous phase. The oil phase was added slowly to the aqueous phase, while the mixture was homo-mixed at 7000 rpm for 3 minutes.

Comparative Example 1 contained 0.4 wt % of salicylic acid, an acidic substance known to have an excellent effect on the exfoliation of keratin. The reason why salicylic acid was added in an amount of 0.4 wt % is that this concentration is the maximum limit usable in cosmetics. Comparative Example 2 contained 0.1 wt % of papain, Example 1 contained papain and theanine, Example 2 contained papain and N-acetyl glucosamine, and Example 3 contained all papain, theanine and N-acetyl glucosamine. A group containing no effective substance was used as a control group.

TABLE 1

| Components | Comparative Example 1 | Comparative Example 2 | Example 1 | Example 2 | Example 3 | Control group |
|---|---|---|---|---|---|---|
| Purified water | Balance | Balance | Balance | Balance | Balance | Balance |
| Squalane | 5.0 | 5.0 | 5.0 | 5.0 | 5.0 | 5.0 |
| Polysorbate 60 | 0.5 | 0.5 | 0.5 | 0.5 | 0.5 | 0.5 |
| Xanthan gum | 1.0 | 1.0 | 1.0 | 1.0 | 1.0 | 1.0 |
| Salicylic acid | 0.4 | — | — | — | — | — |
| Papain | — | 1.0 | 1.0 | 1.0 | 1.0 | — |
| Theanine | | | 1.0 | | 1.0 | — |
| N-acetyl glucosamine | | | | 1.0 | 1.0 | — |

Test Example 1

In order to examine the keratin-exfoliating effects of the above-prepared Examples 1-3 and Comparative Example 1-2, the following test was carried out. The test was carried out on 19 persons in the 20-30-year age group for a period from Feb. 2, 2006 to Feb. 16, 2006 in the following manner.

1. A forearm was washed, and then 6 sites having a size of 4×4 cm² were selected on the washed forearm.

2. 20 mm-diameter filter paper was loaded with 100 μl of dansyl chloride (in triglyceride oil) and then attached to the test sites.

3. The filter paper was stained with a fluorescent dye and stabilized for 24 hours, and then 32 μl of each of the samples was applied on each of the test sites two times every day (one subject applied the sample by 20 times rolling).

4. The fluorescence of the horny layer was photographed under UV light every day in a condition in which other lights were blocked.

<Photographing Conditions>

On the manual mode of a digital camera, iris: 3.5, and shutter speed: 5.

<Method for Evaluating Keratin-Exfoliating Ability)

A forearm was stained with a fluorescent dye, and then the keratin-exfoliating ability of each of the samples was analyzed based on the ratio of decrease in fluorescent intensity.

Fluorescent intensity was objectively analyzed using the image-pro software.

Figure 2:
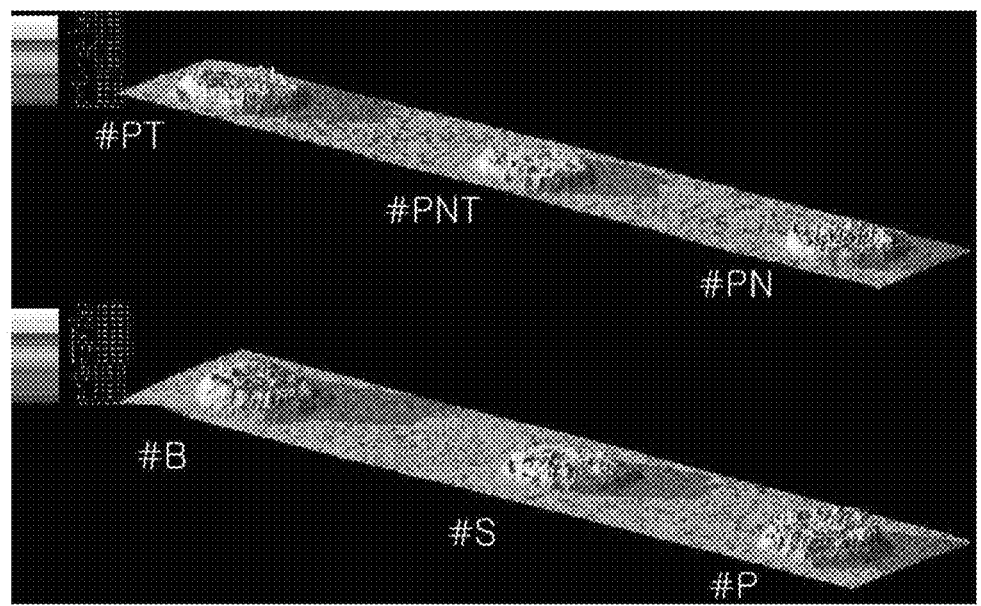
FIG. 2 is a three-dimensional image made using the image-pro software and shows the fluorescent intensity of keratin at sites applied with cosmetic compositions prepared Examples 1 to 3 and Comparative Examples 1 and 2. #S Comparative Example 1, #P: Comparative Example 2, #PT: Example 1, #PN: Example 2, #PNT: Example 3, and #B: control.
Figure 3:
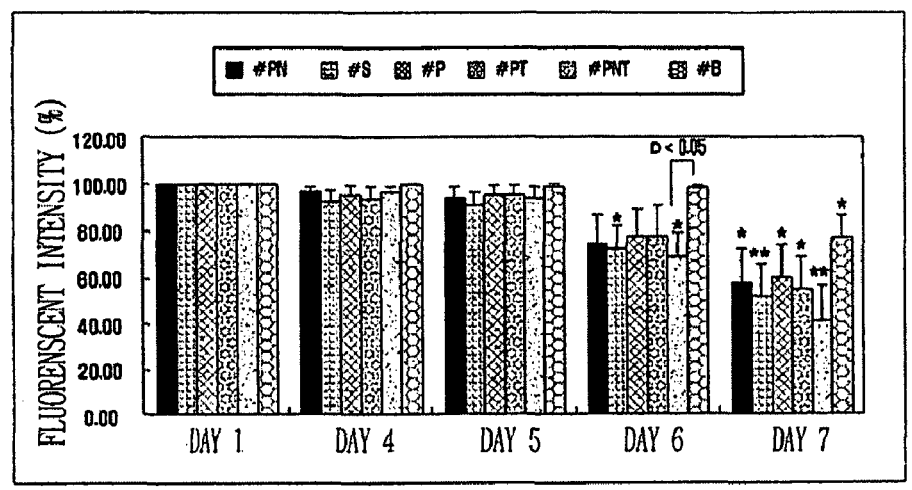
FIG. 3 is a graphic diagram showing the quantitative comparison of keratin exfoliation ability between cosmetic compositions prepared Examples 1 to 3 and Comparative Examples 1 and 2. #S: Comparative Example 1, #P: Comparative Example 2, #PT: Example 1, #PN: Example 2, #PNT: Example 3, and #B: control.

Significant difference was analyzed using t-test ($p<0.05$), ANOVA test and technical statistical analysis, and the analysis results are shown in FIGS. 1 to 3.

FIG. 1 is a photograph made by staining keratin with a fluorescent dye, applying samples on the stained keratin and photographing the samples, in order to examine the keratin-exfoliating abilities of the cosmetic compositions prepared in Examples 1 to 3 and Comparative Examples 1 and 2. In FIG. 1, deep fluorescence means that the exfoliation of keratin is relatively insufficient.

FIG. 2 is a three-dimensional image made using the image-pro software and shows the fluorescent intensity of keratin at sites applied with the cosmetic compositions prepared Examples 1 to 3 and Comparative Examples 1 and 2.

FIG. 3 is a graphic diagram showing the quantitative comparison of keratin exfoliation ability between the cosmetic compositions prepared Examples 1 to 3 and Comparative Examples 1 and 2.

From the results in FIGS. 1 to 3, it could be seen that Examples 1-3 containing papain in combination with theanine and/or N-acetyl glucosamine had an excellent effect on the exfoliation of keratin compared to Comparative Example 1 containing papain alone, and particularly, Example 3 containing all papain, theanine and N-acetyl glucosamine had the most excellent effect on the exfoliation of keratin.

Test Example 2

In order to examine the one-day lasting properties of keratin exfoliation of Example 1 and Comparative Example 1, a test was performed in the same manner as in Test Example 1. However, in order to focus a short-term effect, each of the cosmetic samples was applied in an amount of 64 µl, and fluorescent intensity was measured at varying time points, and observation was performed for 24 hours. The test results are shown in FIG. 4.

Figure 4:
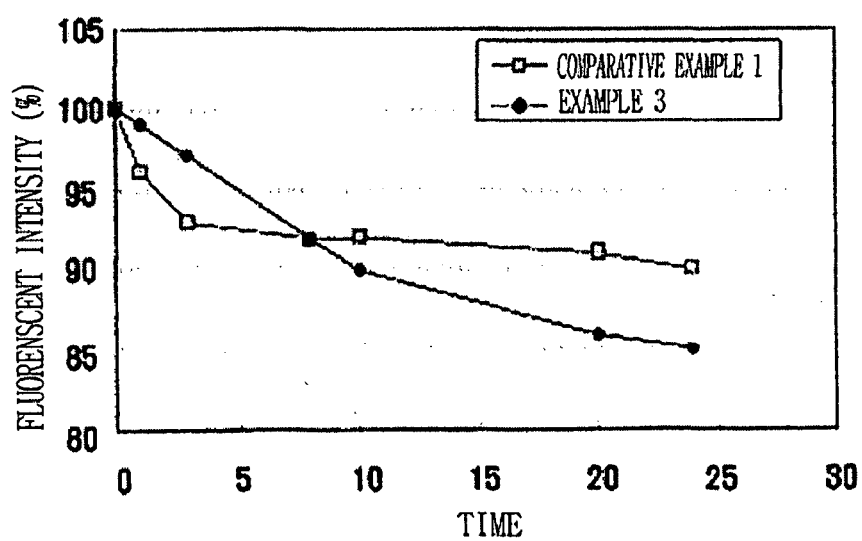
FIG. 4 is a graphic diagram showing the comparison of the lasting ability of keratin exfoliation between cosmetic compositions prepared in Comparative Example 1 and Example 3.

From FIG. 4, it could be seen that, in the case of Comparative Example 1, the exfoliation of a large amount of keratin occurred for an initial period of 3 hours, but after that, the exfoliation of keratin did not substantially occur. However, it could be seen that, in the case of Example 3, the exfoliation of keratin was lasting for 24 hours. Rapid keratin exfoliation for a short period of time in the case of Comparative Example 1 can cause high skin irritation by salicylic acid, but it can be seen that, in the case of Example 3, the keratin-exfoliating effect is lasting, because the exfoliation of keratin is caused by skin-friendly protein enzymes, not by acidic chemical substances such as salicylic acid.

Test Example 3

Figure 5:
FIG. 5 is a cross-sectional photograph showing the change of the skin, which appears upon the application of a cosmetic composition prepared in Example 3.
Figure 5:
Figure 5:
Figure 6:
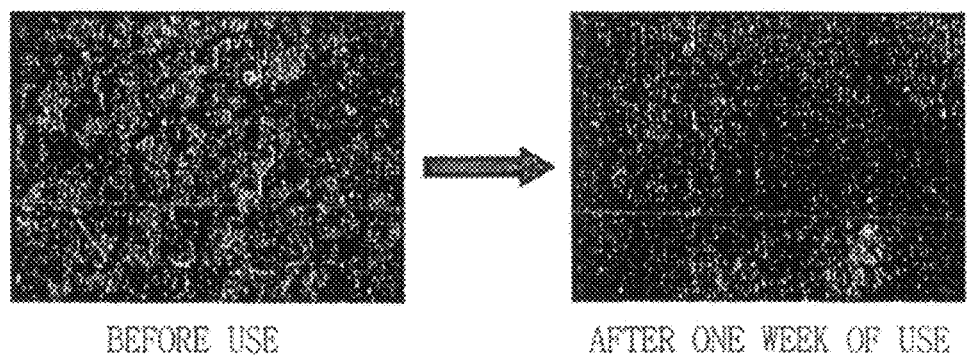
FIG. 6 is a microscopic photograph showing the change of the skin, which appears upon the application of the inventive cosmetic composition.

In order to visually observe the degree of one-week exfoliation of keratin, the cosmetic composition prepared in Example 3 was applied on the skin for one week, and then the cross section of the skin was photographed. The test results are shown in FIGS. 5 and 6. To photograph the cross section of the skin, the H&E staining method was used. Specifically, the skin sample was subjected to frozen section and then stained with hematoxylin. The stained sample was observed with a microscope. FIG. 5 is a photograph showing the cross section of the skin before and after applying the cosmetic composition of Example 3. From FIG. 5, it can be seen that the amount of keratin was significantly reduced after one week of the application of the cosmetic composition of Example 3. FIG. 6 is a microscopic photograph of the front of the skin. From FIG. 6, it can be seen that the skin, which showed hyperkeratinization before the application of the cosmetic composition, was changed to a smooth and uniform state after the application of the cosmetic composition. Through the above test, the keratin-exfoliating effect of the cosmetic composition could be visually confirmed.

INDUSTRIAL APPLICABILITY

As described above, the present invention provides the cosmetic composition for exfoliating keratin, which contains, as active ingredients, papain, theanine and/or N-acetyl glucosamine, and thus maintains skin homeostasis and, at the same time, effectively exfoliates skin keratin and maintains health.

The invention claimed is:

1. A cosmetic composition for exfoliating skin keratin, which contains, as active ingredients, papain, theanine and N-acetyl glucosamine.

2. The cosmetic composition of claim 1, wherein the papain is contained in an amount of 0.1-5.0 wt % based on the total weight of the composition.

3. The cosmetic composition of claim 1, wherein the theanine is contained in an amount of 0.1-5.0 wt % based on the total weight of the composition.

4. The cosmetic composition of claim 1, wherein the N-acetyl glucosamine is contained in an amount of 0.1-5.0 wt % based on the total weight of the composition.

* * * * *